(12) United States Patent
Garcia Molina et al.

(10) Patent No.: US 10,137,276 B2
(45) Date of Patent: Nov. 27, 2018

(54) SYSTEM AND METHOD FOR SLEEP SESSION MANAGEMENT BASED ON SLOW WAVE SLEEP ACTIVITY IN A SUBJECT

(71) Applicants: KONINKLIJKE PHILIPS N.V., Eindhoven (NL); WISCONSIN ALUMNI RESEARCH FOUNDATION, Madison, WI (US)

(72) Inventors: Gary Nelson Garcia Molina, Madison, WI (US); Giulio Tononi, Verona, WI (US); Sander Theodoor Pastoor, Utrecht (NL); Stefan Pfundtner, Eindhoven (NL); Brady Alexander Riedner, Middleton, WI (US); Michele Bellesi, Madison, WI (US)

(73) Assignee: Koninklijke Philips N.V., Eindhoven (NL)

( * ) Notice: Subject to any disclaimer, the term of this patent is extended or adjusted under 35 U.S.C. 154(b) by 443 days.

(21) Appl. No.: 14/784,782

(22) PCT Filed: Apr. 20, 2014

(86) PCT No.: PCT/IB2014/060867
§ 371 (c)(1),
(2) Date: Oct. 15, 2015

(87) PCT Pub. No.: WO2014/170881
PCT Pub. Date: Oct. 23, 2014

(65) Prior Publication Data
US 2016/0058970 A1  Mar. 3, 2016

Related U.S. Application Data

(60) Provisional application No. 61/813,714, filed on Apr. 19, 2013.

(51) Int. Cl.
*A61M 21/02* (2006.01)
*A61B 5/0476* (2006.01)
(Continued)

(52) U.S. Cl.
CPC ............. *A61M 21/02* (2013.01); *A61B 5/048* (2013.01); *A61B 5/0476* (2013.01);
(Continued)

(58) Field of Classification Search
CPC ............ A61M 21/02; A61M 2205/502; A61M 2205/3303; A61M 2230/63;
(Continued)

(56) References Cited

U.S. PATENT DOCUMENTS

2006/0293608 A1  12/2006  Rothman et al.
2008/0234785 A1   9/2008  Nakayama et al.
(Continued)

FOREIGN PATENT DOCUMENTS

EP  2460464 A1  6/2012
GB  2233764 A   1/1991
(Continued)

OTHER PUBLICATIONS

Achermann et al, "A Model of Human Sleep Homeostasis Based on EEG Slow-Wave Activity: Quantitative Comparison of Data and Simulations", Brain Research Bulletin, vol. 31, 1993, pp. 97-113.
(Continued)

*Primary Examiner* — Kaylee Wilson

(57) ABSTRACT

The present disclosure pertains to a system and method for managing a sleep session of a subject. Managing the sleep session is based on slow wave activity in the subject during the sleep session. Slow wave activity is related to sleep pressure. Sleep pressure dissipates and/or decreases as the subject sleeps. The dissipation dynamics depend on a given subject. The manner in which dissipation occurs regulates
(Continued)

the length of the given sleep session and is linked to the temporal dynamics of slow wave activity. The system is configured to determine a metric indicating sleep pressure dissipation and, responsive to the determined sleep pressure dissipation metric indicating that sleep pressure dissipation has reached a dissipation threshold level during the sleep session, wake the subject.

15 Claims, 6 Drawing Sheets

(51) Int. Cl.
*A61B 5/048* (2006.01)
*A61B 5/00* (2006.01)
*A61N 1/04* (2006.01)
*A61N 1/36* (2006.01)
*A61M 21/00* (2006.01)

(52) U.S. Cl.
CPC .......... *A61B 5/4812* (2013.01); *A61N 1/0456* (2013.01); *A61N 1/0484* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2021/0083* (2013.01); *A61M 2205/3303* (2013.01); *A61M 2205/502* (2013.01); *A61M 2230/005* (2013.01); *A61M 2230/06* (2013.01); *A61M 2230/10* (2013.01); *A61M 2230/42* (2013.01); *A61M 2230/63* (2013.01); *A61N 1/36025* (2013.01)

(58) Field of Classification Search
CPC .......... A61M 2230/42; A61M 2230/10; A61M 2230/06; A61M 2230/005; A61M 2021/0083; A61M 21/00; A61B 5/0476; A61B 5/048; A61B 5/4812; A61N 1/0456; A61N 1/0484
See application file for complete search history.

(56) References Cited

U.S. PATENT DOCUMENTS

| | | |
|---|---|---|
| 2009/0082639 A1 | 3/2009 | Pittman et al. |
| 2011/0230790 A1 | 9/2011 | Kozlov |
| 2012/0251989 A1 | 10/2012 | Wetmore et al. |
| 2012/0253220 A1* | 10/2012 | Rai .................. A61B 5/0476 600/544 |
| 2012/0253221 A1 | 10/2012 | Hamaguchi et al. |

FOREIGN PATENT DOCUMENTS

| | | |
|---|---|---|
| JP | 2011159108 A | 8/2011 |
| RU | 2214931 C2 | 10/2003 |
| RU | 2304988 C2 | 8/2007 |
| UA | 50019 A | 10/2002 |

OTHER PUBLICATIONS

Landsness et al, "Antidepressant Effects of Selective Slow Wave Sleep Deprivation in Major Depression: A High-Density EEG Investigation", Journal of Psychiatric Research, vol. 45, No. 8, 2011, pp. 1019-1026.

Achermann et al, "Simulation of Human Sleep: Ultradian Dynamics of Electroencephalographic Slow-Wave Activity", Journal of Biological Rhythms, vol. 5, No. 2, 1990, pp. 141-157.

Massimini et al, "Triggering Sleep Slow Waves by Transcranial Magnetic Stimulation", PNAS, vol. 104, No. 20, 2007, pp. 8496-8501.

Tononi et al, "Enhancing Sleep Slow Waves With Natural Stimuli", Medicamundi, vol. 54, No. 2, 2010, pp. 82-88.

Munch et al, "Wavelength-Dependent Effects of Evening Light Exposure on Sleep Architecture and Sleep EEG Power Density in Men", American Journal Physiological Society, vol. 290, 2006, pp. R1421-R1428.

Borbely, "A Two Process Model of Sleep Regulation", Human Neurobiology, vol. 1, No. 3, 1982, pp. 195-204.

Landsness, Eric C., "Sleep-dependent improvement in visuomotor learning: a causal role for slow waves", Sleep vol. 32, issue 10, pp. 1273-1284, Oct. 2009.

* cited by examiner

SYSTEM AND METHOD FOR SLEEP SESSION MANAGEMENT BASED ON SLOW WAVE SLEEP ACTIVITY IN A SUBJECT

CROSS-REFERENCE TO PRIOR APPLICATIONS

This application is the U.S. National Phase application under 35 U.S.C. § 371 of International Application Serial No. PCT/IB2014/060867, filed on Apr. 20, 2014, which claims the benefit of U.S. Application Ser. No. 61/813,714, filed on Apr. 19, 2013. These applications are hereby incorporated by reference herein.

BACKGROUND

1. Field

The present disclosure pertains to a system and method for managing a sleep session of a subject. Managing the sleep session is based on slow wave activity in the subject prior to and/or during the sleep session.

2. Description of the Related Art

Systems for monitoring sleep are known. Sensory stimulation during sleep is known. Sensory stimulation during sleep is often applied continuously and/or at intervals that do not correspond to sleeping patterns of a subject. The present disclosure overcomes deficiencies in prior art systems.

SUMMARY

Accordingly, one or more aspects of the present disclosure relate to a system configured to manage a current sleep session of a subject. The system comprises one or more sensory stimulators, one or more sensors, and one or more processors. The one or more sensory stimulators are configured to provide sensory stimuli to the subject. The one or more sensors are configured to generate output signals conveying information related to a current sleep stage of the subject during the current sleep session. The one or more processors are configured to execute computer program modules. The computer program modules comprise a sleep parameter module, a sleep pressure dissipation module, and a control module. The sleep parameter module may be configured to determine one or more sleep parameters based on the output signals. The one or more parameters include a sleep pressure. The sleep pressure is related to slow wave activity in the subject prior to and/or during the current sleep session. The sleep pressure dissipation module is configured to determine a metric indicating sleep pressure dissipation in the subject during the current sleep session. The metric is determined based on the sleep pressure determination. The control module is configured such that, responsive to the determined sleep pressure dissipation metric indicating that sleep pressure dissipation has reached a dissipation threshold level during the current sleep session, the control module controls the one or more sensory stimulators to generate a waking stimulus. The waking stimulus comprises sensory stimulation configured to wake the subject from sleep.

Yet another aspect of the present disclosure relates to a method for managing a current sleep session of a subject with a management system. The system comprises one or more sensory stimulators, one or more sensors, and one or more processors configured to execute computer program modules. The computer program modules comprise a sleep parameter module, a sleep pressure dissipation module, and a control module. The method comprises generating output signals conveying information related to a current sleep stage of the subject during the current sleep session with the one or more sensors; determining, with the sleep parameter module, one or more sleep parameters based on the output signals, the one or more parameters including a sleep pressure, the sleep pressure being related to slow wave activity in the subject during the current sleep session; determining, with the sleep pressure dissipation module, a metric indicating sleep pressure dissipation in the subject during the current sleep session, the metric determined based on the sleep pressure determination; and, responsive to the determined sleep pressure dissipation metric indicating that sleep pressure dissipation has reached a dissipation threshold level during the current sleep session, controlling, with the control module, the one or more sensory stimulators to generate a waking stimulus, wherein the waking stimulus comprises sensory stimulation configured to wake the subject from sleep.

Still another aspect of present disclosure relates to a system configured to manage a current sleep session of a subject. The system comprises means for providing sensory stimuli to the subject; means for generating output signals conveying information related to a current sleep stage of the subject during the current sleep session; means for determining one or more sleep parameters based on the output signals, the one or more parameters including a sleep pressure, the sleep pressure being related to slow wave activity in the subject during the current sleep session; means for determining a metric indicating sleep pressure dissipation in the subject during the current sleep session, the metric determined based on the sleep pressure determination; and means for, responsive to the determined sleep pressure dissipation metric indicating that sleep pressure dissipation has reached a dissipation threshold level during the current sleep session, controlling the means for providing sensory stimuli to generate a waking stimulus, wherein the waking stimulus comprises sensory stimulation configured to wake the subject from sleep.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
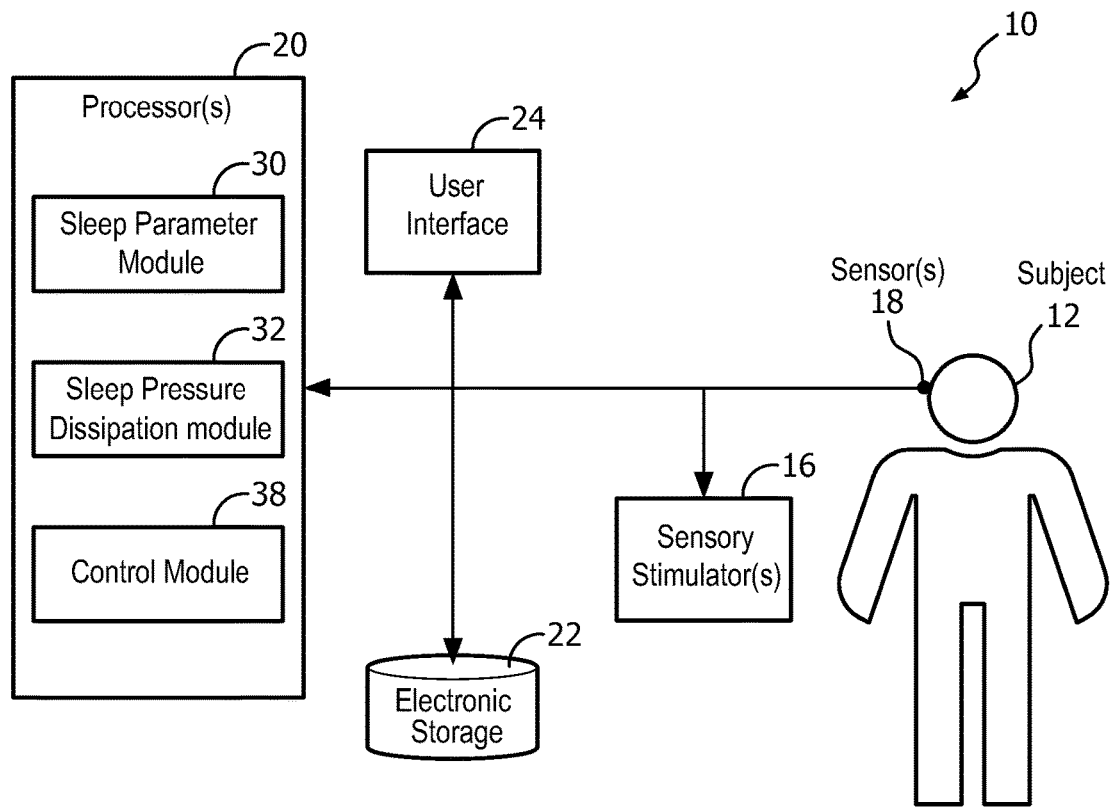
FIG. 1 is a schematic illustration of a system configured to manage a sleep session of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to manage a current sleep session of a subject 12. Most people acknowledge the importance of sleep but many people do not get a healthy amount of sleep. The aspiration for healthier sleep is balanced against demands on time. System 10 manages the current sleep session based on slow wave activity (SWA) in subject 12 during the current sleep session. SWA corresponds to the power of the EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated from an electroencephalogram (EEG) for subject 12 during a given sleep session.

SWA is related to sleep pressure. Sleep pressure may be thought of as a need for sleep in a given subject. The higher the SWA is, the higher the need for sleep is. The decrease in SWA throughout a sleep episode reflects the dissipation of sleep need. Sleep pressure dissipates and/or decreases as subject 12 sleeps. The dissipation dynamics depend on the given subject. The manner in which dissipation occurs regulates the length of a given sleep session and is linked to the temporal dynamics of SWA. System 10 is configured to determine a metric indicating sleep pressure dissipation and, responsive to the determined sleep pressure dissipation metric indicating that sleep pressure dissipation has reached a dissipation threshold level during the current sleep session, wake subject 12.

Figure 2:
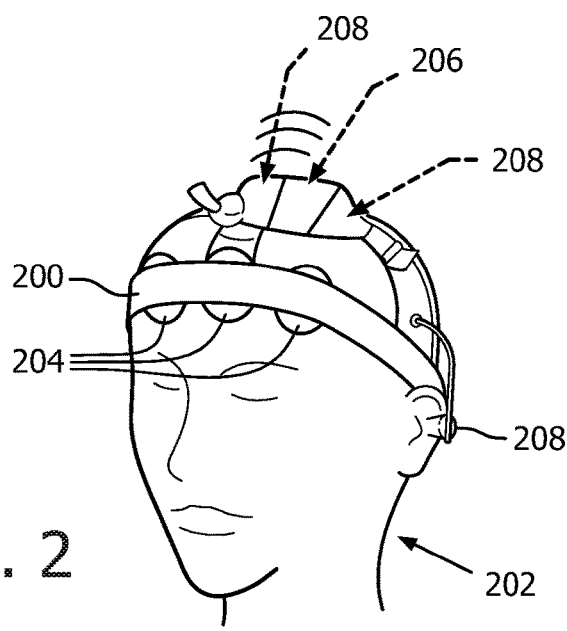
FIG. 2 illustrates a headset worn by a subject and includes sensing electrodes, a bio-signal amplifier, and a wireless audio device.

In some embodiments, system 10 may comprise one or more of a sensory stimulator 16, a sensor 18, a processor 20, electronic storage 22, a user interface 24, and/or other components. In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 2 illustrates a headset 200 worn by a subject 202 and includes sensing electrodes 204, a bio-signal amplifier 206, and a wireless audio device 208. Sensing electrodes 204 and bio-signal amplifier 206 may be represented, for example, by sensor 18 in FIG. 1. Wireless audio device 208 may be represented, for example, by sensory stimulator 16 shown in FIG. 1.

Returning to FIG. 1, sensory stimulator 16 is configured to provide sensory stimuli to subject 12. Sensory stimulator 16 is configured to provide sensory stimulation to subject 12 prior to the current sleep session, during the current sleep session, and/or at other times. For example, sensory stimulator 16 may be configured to provide sensory stimuli to subject 12 during slow wave sleep in the current sleep session. Sensory stimulator 16 may be configured to provide sensory stimulation to subject 12 during the current sleep session to induce and/or adjust SWA in subject 12. In some embodiments, sensory stimulator 16 may be configured such that adjusting includes increasing, decreasing, and/or other adjustment of SWA in subject 12.

In some embodiments, sensory stimulator 16 may be configured to induce and/or adjust SWA through non-invasive brain stimulation and/or other methods. Sensory stimulator 16 may be configured to induce and/or adjust SWA through non-invasive brain stimulation using sensory stimuli. The sensory stimuli include odors, sounds, visual stimulation, touches, tastes, and/or other stimuli. For example, transcranial magnetic stimulation may be applied to subject 12 to trigger, increase, and/or decrease SWA. As another example, sensory stimulator 16 may be configured to induce and/or adjust SWA via auditory stimulation of subject 12. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

In some embodiments, sensory stimulator 16 is configured to generate a waking stimulus. The waking stimulus includes sensory stimulation configured to wake subject 12 from sleep. For example, sensory stimulator 16 may generate an auditory alarm to wake subject 12. As another example, sensory stimulator 16 may increase an ambient lighting level to wake subject 12.

Sensor 18 is configured to generate output signals conveying information related to a current sleep stage of subject 12. The current sleep stage of subject 12 may correspond to one or more of non-rapid eye movement (NREM) stage N1, stage N2, or stage N3 sleep, and/or rapid eye movement (REM) sleep. In some embodiments, NREM stage 3 or stage 2 sleep may be slow wave sleep. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to a current sleep stage of the subject indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location in communication with subject 12, this is not intended to be limiting. Sensor 18 may include sensors disposed in a plurality of locations, such as for example, within (or in communication with) sensory stimulator 16, and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program modules. The one or more computer program modules may comprise one or more of a sleep parameter module 30, a sleep pressure dissipation module 32, a control module 38, and/or other modules. Processor 20 may be configured to execute modules 30, 32, and/or 38 by software; hardware; firmware; some combination of software, hardware, and/or firmware; and/or other mechanisms for configuring processing capabilities on processor 20.

It should be appreciated that although modules 30, 32, and 38 are illustrated in FIG. 1 as being co-located within a single processing unit, in implementations in which processor 20 comprises multiple processing units, one or more of modules 30, 32, and/or 38 may be located remotely from the other modules. The description of the functionality provided by the different modules 30, 32, and/or 38 described below is for illustrative purposes, and is not intended to be limiting, as any of modules 30, 32, and/or 38 may provide more or less functionality than is described. For example, one or more of modules 30, 32, and/or 38 may be eliminated, and some or all of its functionality may be provided by other modules 30, 32, and/or 38. As another example, processor 20 may be configured to execute one or more additional modules that may perform some or all of the functionality attributed below to one of modules 30, 32, and/or 38.

Sleep parameter module 30 is configured to determine one or more sleep parameters based on the output signals from sensor 18. The one or more sleep parameters may include a sleep stage, a timing for delivery of sensory stimulation, a sleep pressure, the power in the slow activity band (0.5-4.5 Hz) or other frequency bands, and/or other parameters. The sleep pressure is related to SWA in subject 12. Sleep parameter module 30 may identify SWA in subject 12 based on an analysis of the information conveyed by the output signals of sensor 18. The analysis may include generating and/or monitoring an EEG during a sleep session of subject 12. In some embodiments, SWA may be quantified by sleep parameter module 30 via the EEG spectral power in the 0.5-4.5 Hz frequency range, for example. Sleep parameter module 30 may determine the sleep pressure based on the SWA. In some embodiments, sleep parameter module 30 may be configured to generate a hypnogram based on the determined parameters. The EEG and/or the hypnogram may be displayed, for example, by user interface 24.

In some embodiments, sleep parameter module 30 may be configured to identify sleep stages (e.g., N1, N2, N3) while subject 12 is sleeping. In some embodiments, sleep parameter module 30 may determine a timing for delivery of sensory stimulation. In some embodiments, the timing for delivery of sensory stimulation may correspond to sleep stages associated with slow wave activity (e.g., N2, N3). For example, sleep parameter module 30 may be configured to determine a timing for delivery of sensory stimulation such that the determined timing corresponds to sleep stages N2 and N3 while subject 12 is sleeping. Sleep parameter module 30 may be configured to determine a timing for delivery of sensory stimulation such that the determined timing corresponds to sleep stages associated with slow wave activity because the likelihood for slow-wave induction, and/or adjustment during the specific sleep stage may be comparatively higher than in other sleep stages, the user may be less likely to be awakened by the sensory stimuli, and/or for other reasons.

Sleep pressure dissipation module 32 is configured to determine the metric indicating sleep pressure dissipation in subject 12 during the current sleep session. The metric is determined based on the sleep pressure determination, and/or other information. In some implementations, the metric may be related to the sleep pressure dissipation (e.g., a derivative of the sleep pressure dissipation and/or a final sleep pressure). In some embodiments, the metric may be the sleep pressure dissipation. In some embodiments, sleep pressure dissipation module 32 is configured to determine the sleep pressure dissipation metric based on a model that characterizes the relation between the SWA and the sleep pressure (S) in subject 12. In some embodiments, the model may include equations (1) and (2) shown below.

$$\frac{dS(t)}{dt} = -g_c SWA(t) \quad (1)$$

$$\frac{dSWA(t)}{dt} = r_c \cdot SWA(t) \cdot \left(1 - \frac{SWA(t)}{S(t)}\right) - f_c \cdot SWA(t) \cdot REMT(t) \quad (2)$$

The instantaneous rate of decrease is sleep pressure (dS(t)/dt) is related to SWA by a proportionality constant $g_c$. The instantaneous rate of change in SWA (dSWA(t)/dt) is, in turn, related to the current value of the sleep pressure (S(t)) and SWA (SWA(t)) as defined in equation (2), where $r_c$ is a SWA-rise constant, $f_c$ is a SWA-fall constant, and REMT(t) is a function related to SWA. In some embodiments, the model that characterizes the relation between the SWA and the sleep pressure may be determined based on previous sleep sessions of subject 12, based on information received via user interface 24, and/or based on other information. In some embodiments, the model may be programmed at manufacture.

Figure 3:
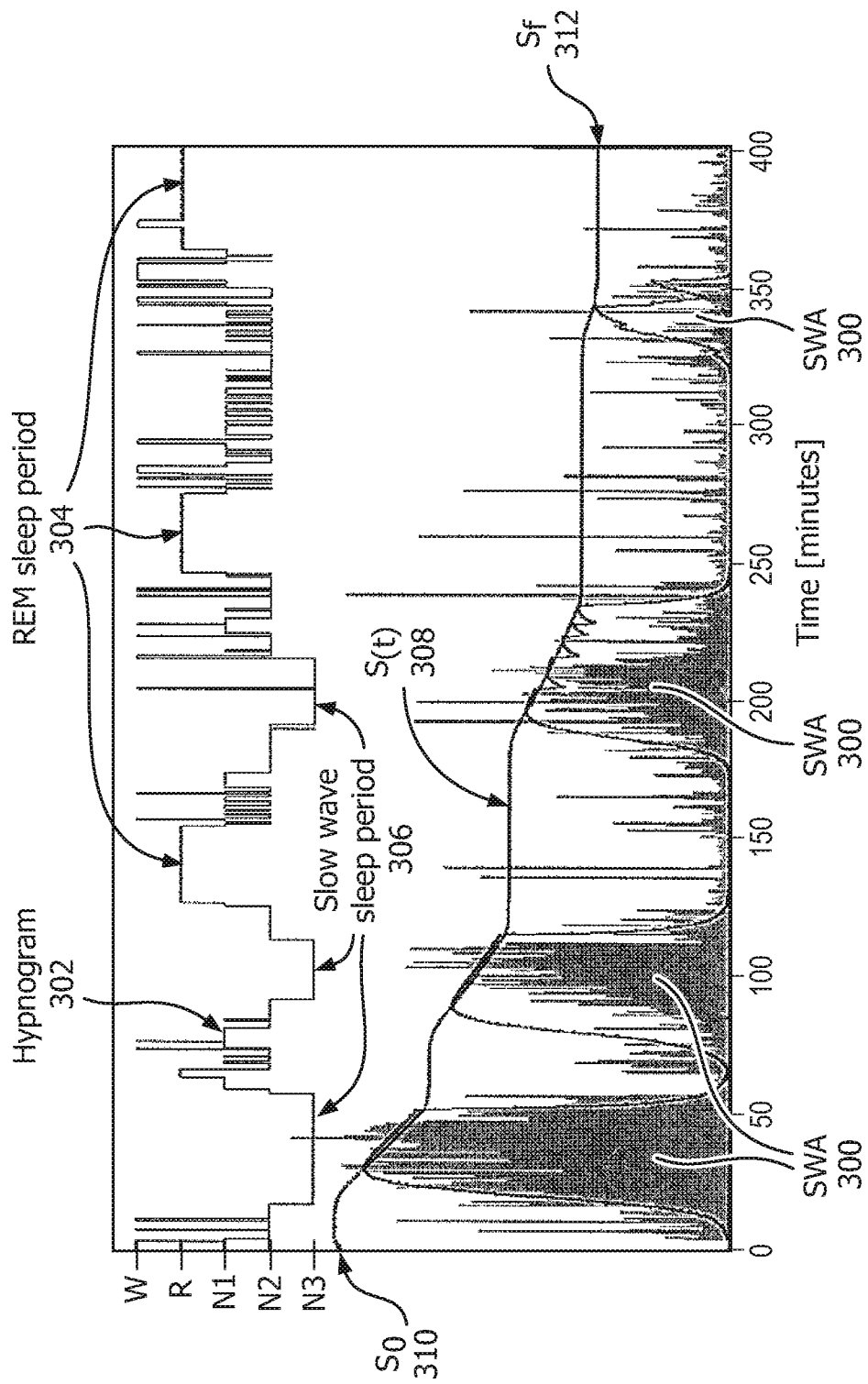
FIG. 3 illustrates slow wave activity, a hypnogram showing REM sleep periods and slow wave sleep periods, and sleep pressure as a function of time during a sleep session.

For example, FIG. 3 illustrates SWA 300, a hypnogram 302 showing REM sleep periods 304 and slow wave sleep periods 306, and sleep pressure as a function of time, S(t) 308, during a sleep session. Sleep pressure as a function of time 308 may be determined, for example, according to the model described above by equations 1 and 2. An initial sleep pressure, $S_o$ 310, and a final sleep pressure $S_f$ 312, are also shown in FIG. 3. Sleep pressure as a function of time, S(t) 308, decreases from initial sleep pressure 310 to final sleep pressure 312 during the sleep session. FIG. 3 illustrates that sleep pressure as a function of time 308 decreases faster during periods of SWA 300 and/or slow wave sleep 306.

Returning to FIG. 1, the description of the model presented herein is not intended to be limiting. The model that characterizes the relation between the SWA and the sleep pressure may include any model configured to establish a relationship between the SWA and the sleep pressure.

Control module 38 is configured to, responsive to the determined sleep pressure dissipation metric indicating that sleep pressure dissipation has reached a dissipation threshold level during the current sleep session, control sensory stimulator 16 to generate the waking stimulus. In some embodiments, control module 38 may be configured such that the determined sleep pressure dissipation metric indicates that sleep pressure dissipation has reached the dissipation threshold level during the current sleep session when no further and/or substantial decline in the sleep pressure can be expected. In some embodiments, control module 38 is configured to determine the dissipation threshold level based on information from one or more previous sleep sessions of subject 12, based on information from the current sleep session, and/or based on other information. In some embodiments, the dissipation threshold level may be considered to be reached as soon as the dissipation threshold level is attained and/or exceeded. In some embodiments, the dissipation threshold level may considered to be reached responsive to the dissipation threshold level being attained and/or exceeded for a predetermined period of time. In some embodiments, the dissipation threshold level may be considered to be reached responsive to an average (and/or other mathematical conglomerations) dissipation threshold level being attained or exceeded over a predetermined period of time. The examples above related to reaching the dissipation threshold level are not intended to be limiting. Reaching the dissipation threshold level may include any event that allows system 10 to function as described herein.

Information from one or more previous sleep sessions of subject 12 may include the SWA of subject 12 along with the corresponding hypnogram, and/or other information. Information from one or more previous sleep sessions of subject 12 may include typical values of sleep pressure at the beginning (e.g., $S_o$) and end (e.g., $S_f$) of a sleep session, information related to the decline of sleep pressure (e.g., S(t)) as a function of the SWA, and/or other information. For example, the sleep pressure dissipation metric may be a sleep pressure level at a given time during a sleep session. The dissipation threshold level may be an average value of the final sleep pressure level from two or more previous sleep sessions of subject 12, for example. In some implementations, control module 38 may be configured to determine the dissipation threshold level based on SWA and sleep pressure information from a population of users who correspond to subject 12. For example, age, gender, and/or other factors of users in the population may indicate that the users correspond to subject 12.

Information from the current sleep session may include the sleep pressure as a function of time, and/or other information. In some implementations, the sleep pressure dissipation metric may be the derivative of the sleep pressure as a function of time. The dissipation threshold level may be a value (e.g., a small negative number) of the derivative, for example. Control module 38 may determine that the sleep pressure dissipation metric has reached the dissipation threshold level during the current sleep session responsive to the derivative of the sleep pressure as a function of time reaching the dissipation threshold level.

Figure 4:
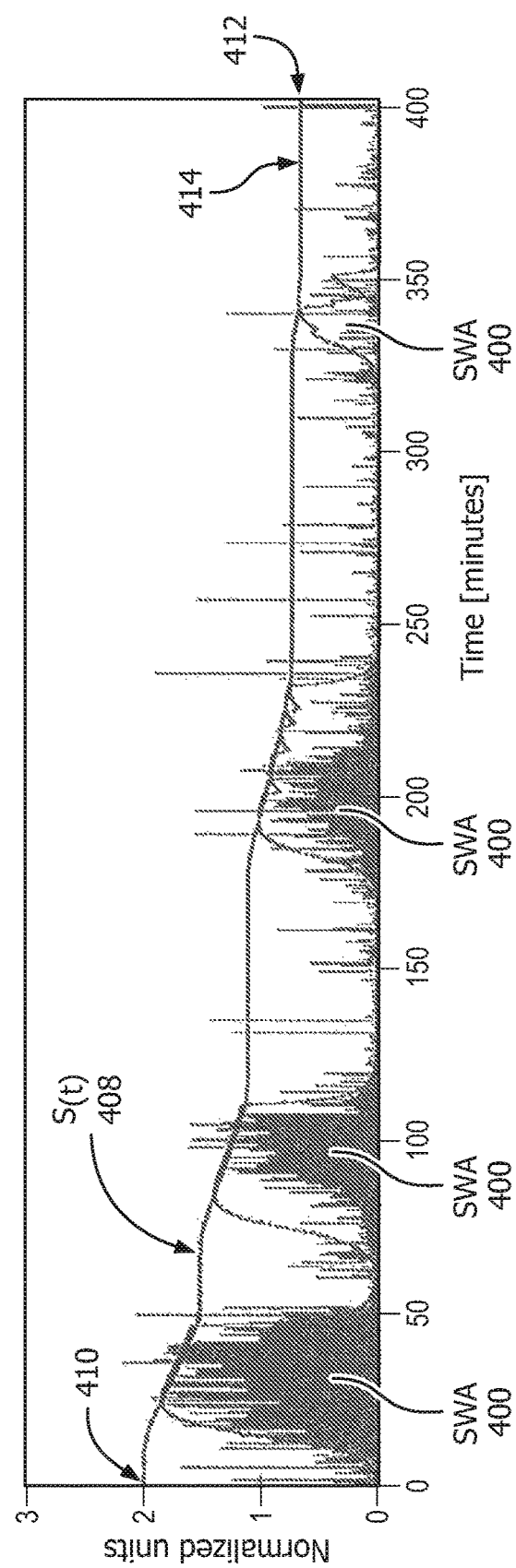
FIG. 4 illustrates slow wave activity and sleep pressure as a function of time during a sleep session.

For example, FIG. 4 illustrates SWA 400 and sleep pressure as a function of time, S(t) 408, during a sleep session. Sleep pressure as a function of time, S(t) 408, decreases from initial sleep pressure 410 to final sleep pressure 412 during the sleep session. FIG. 4 illustrates a sleep interruption point 414 where no further substantial decline in sleep pressure may be expected (e.g., sleep pressure as a function of time 408 is a flat or slightly negatively sloped line).

Returning to FIG. 1, in some embodiments, control module 38 is configured to control sensory stimulator 16 to adjust SWA in subject 12 during the current sleep session such that a sleep session duration meets a sleep session duration target. The sleep session duration may be the length of time subject 12 sleeps during a sleep session. Information related to the sleep session duration target may be received from subject 12 and/or other users via user interface 24, for example. The information related to the sleep session duration target may include a time of day, a length of time, and/or other information. Other users may include a doctor, a care-giver, and/or other users. Control module 38 may be configured to determine the sleep session duration target based on the received information related to the sleep session duration target, based on previous sleep sessions of subject 12, and/or based on other information. Control module 38 may be configured to control sensory stimulator 16 to adjust SWA in subject 12 during the current sleep session such that the sleep session duration meets the sleep session duration target based on the determined sleep session duration target, the determined sleep pressure dissipation metric, the dissipation threshold level, the information from one or more previous sleep sessions of subject 12, and/or other information.

Adjusting SWA in subject 12 while subject 12 is asleep during the current sleep session may include controlling sensory stimulator 16 to increase and/or decrease SWA in subject 12 during sleep. In some embodiments, control module 38 is configured such that controlling sensory stimulator 16 to increase SWA in subject 12 results in an increase in the sleep pressure dissipation and controlling sensory stimulator 16 to decrease slow wave activity in subject 12 results in a decrease in the sleep pressure dissipation. In some embodiments, control module 38 is configured such that a timing for delivery of sensory stimulation is the timing determined by sleep parameter module 30 that corresponds to the sleep stages associated with slow wave activity (e.g., N2, N3).

Figure 5:
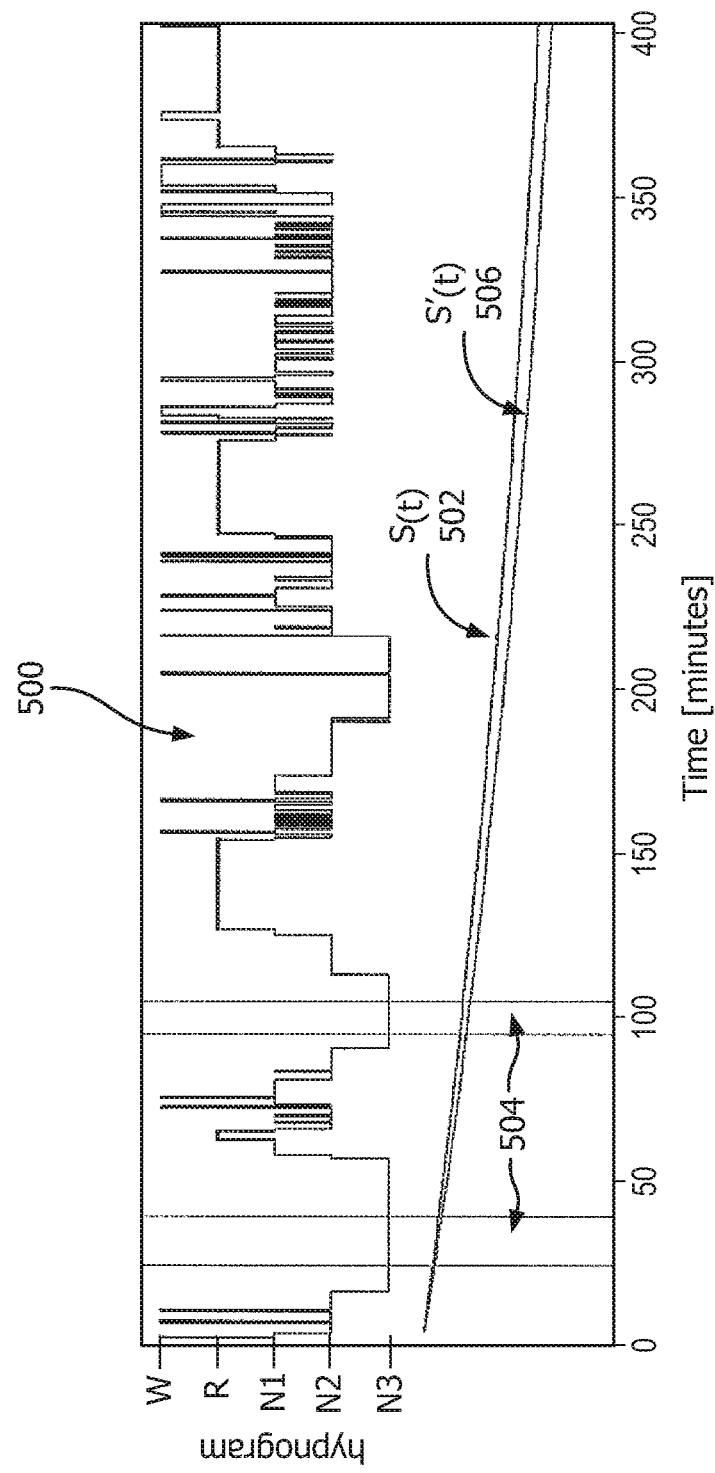
FIG. 5 illustrates a hypnogram and sleep pressure as a function of time during a sleep session.

For example, FIG. 5 illustrates a hypnogram 500 and sleep pressure as a function of time, S(t) 502. S(t) 502 may be determined based on equations (1) and (2) described above, for example. SWA may be increased (e.g., a 5% increase) by the system during periods 504 that correspond to stage N3 sleep. An adjusted sleep pressure as a function of time S'(t) 506, decays faster than S(t) 502. In the example shown in FIG. 5, faster decay of S'(t) 506 may indicate faster sleep pressure dissipation and a shorter time until the sleep pressure dissipation metric reaches the dissipation threshold level.

Returning to FIG. 1, in some embodiments, control module 38 may cause information related to sleep pressure as a function of time, the initial sleep pressure, the final sleep pressure, SWA adjustments, and/or other information from one or more sleep sessions of subject 12 to be stored in electronic storage 22. In some embodiments, control module 38 may be configured to estimate a percentage increase and/or decrease in SWA needed during a current sleep session such that the sleep session duration meets the sleep session duration target. Control module 38 may be configured to estimate the percentage based on sleep pressure as a function of time, the initial sleep pressure, the final sleep pressure, SWA adjustments, and/or other information from the one or more sleep sessions of subject 12. For example, control module 38 may be configured to estimate a percentage increase and/or decrease in SWA needed to reach a given final sleep pressure within a given sleep session duration based on the initial sleep pressure and sleep pressure dissipation as a function of time information from previous sleep sessions of subject 12.

Figure 6:
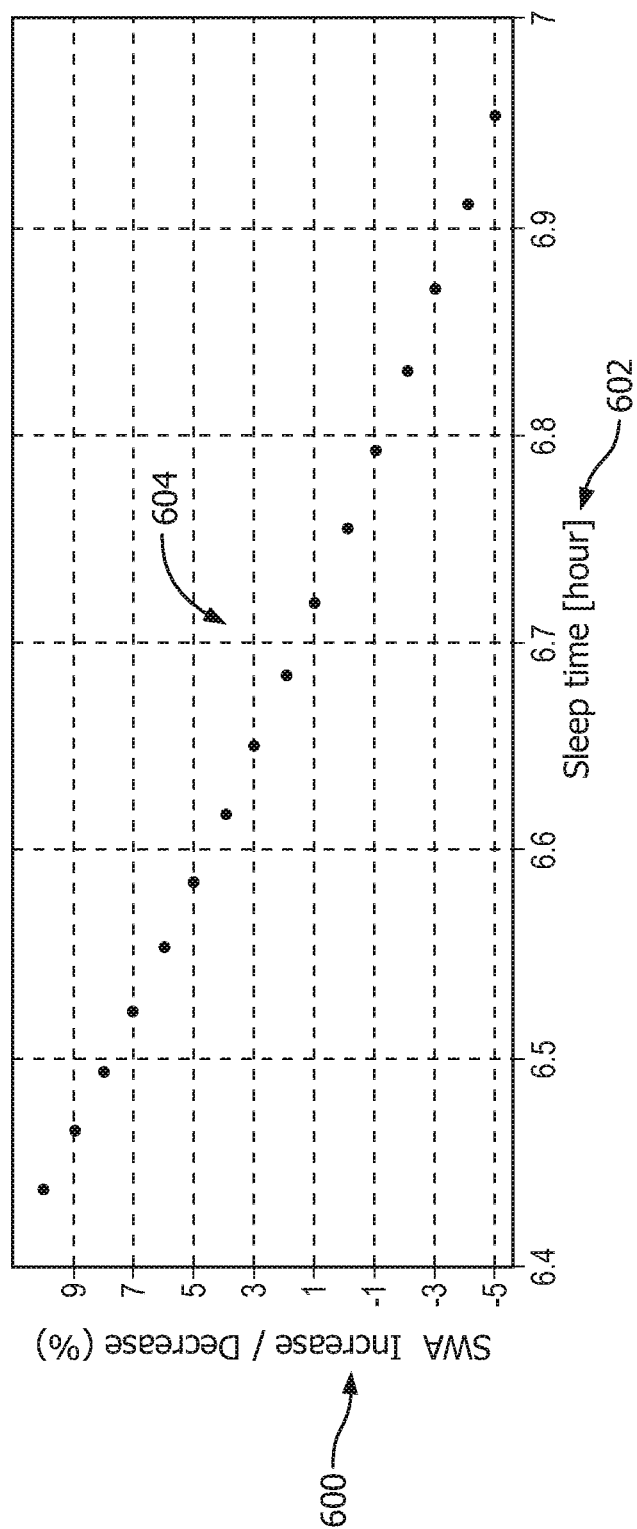
FIG. 6 illustrates an example of a relationship between increased and/or decreased slow wave activity and sleep time for a given subject.

FIG. 6 illustrates an example of a relationship 604 between increased and/or decreased SWA 600 and sleep time 602 for a given subject (e.g., subject 12). In the example shown in FIG. 6, the increase and/or decrease in SWA is relative to a baseline amount of SWA for the given subject determined based on previous sleep sessions of the given subject.

Returning to FIG. 1, control module 38 may control sensory stimulator 16 to provide the sensory stimulation during the current sleep session such that the sensory stimulation does not wake subject 12. For example, control module 38 may control sensory stimulator 16 to provide the sensory stimulation at a low intensity level. In some embodiments, control module 38 is configured to control sensory stimulator 16 to provide sensory stimulation to subject 12 to adjust slow wave activity in subject 12 in an upcoming sleep session while the subject is awake before the upcoming sleep session.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to receive information related to a sleep session duration target for subject 12, and/or other information. User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16, sensory stimulator 16, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
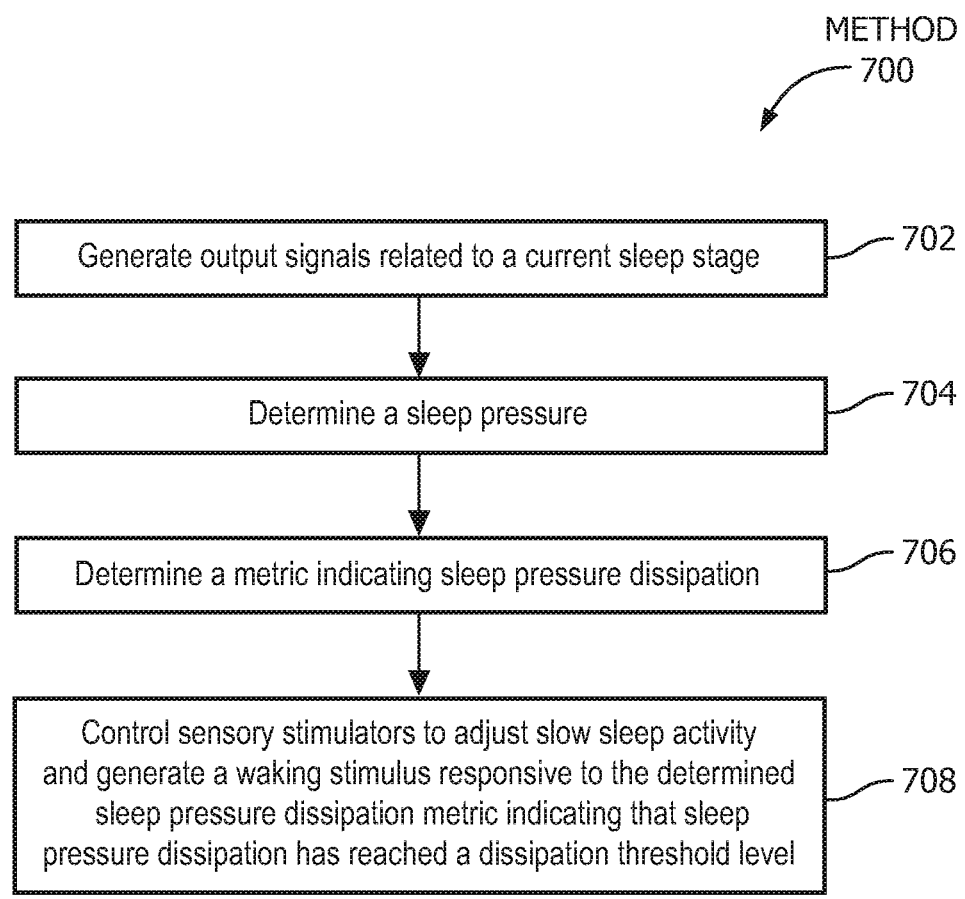
FIG. 7 illustrates a method for managing a sleep session of a subject.

FIG. 7 illustrates a method 700 for managing a current sleep session of a subject with a management system. The system comprises one or more sensory stimulators, one or more sensors, and one or more processors configured to execute computer program modules. The computer program modules comprise a sleep parameter module, a sleep pressure dissipation module, and a control module. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to a current sleep stage of the subject during the current sleep session are generated. In some embodiments, operation 702 is performed by one or more sensors the same as or similar to sensors 18 (shown in FIG. 1 and described herein).

At an operation 704, a sleep pressure is determined. In some embodiments, one or more sleep parameters are determined based on the output signals. The one or more parameters include the sleep pressure. The sleep pressure is related to slow wave activity in the subject during the current sleep session. In some embodiments, operation 704 is performed by a computer program module the same as or similar to sleep parameter module 30 (shown in FIG. 1 and described herein).

At an operation 706, a metric indicating sleep pressure dissipation is determined. The metric indicates sleep pressure dissipation in the subject during the current sleep session. The metric is determined based on the sleep pressure determination. In some embodiments, operation 706 is performed by a computer program module the same as or similar to sleep pressure dissipation module 32 (shown in FIG. 1 and described herein).

At an operation 708, sensory stimulators are controlled to adjust slow wave activity in the subject and generate a waking stimulus responsive to the determined sleep pressure dissipation metric indicating that sleep pressure dissipation has reached a dissipation threshold level. The waking stimulus comprises sensory stimulation configured to wake the subject from sleep. The dissipation threshold level may be determined based on information from one or more previous sleep sessions of the subject, and/or other information.

In some embodiments, operation 708 may include receiving information related to a sleep session duration target for the subject via a user interface, providing sensory stimulation to the subject during the current sleep session to adjust slow wave activity in the subject, and controlling the one or more sensory stimulators to adjust slow wave activity in the subject such that a sleep session duration meets the sleep session duration target. The controlling is based on the sleep session duration target, the determined sleep pressure dissipation metric, and the dissipation threshold level. In some embodiments, controlling the one or more sensory stimulators to increase slow wave activity in the subject results in an increase in the sleep pressure dissipation metric and controlling the one or more sensory stimulators to decrease slow wave activity in the subject results in a decrease in the sleep pressure dissipation metric. In some embodiments, the one or more sensory stimulators are controlled to provide sensory stimulation to the subject to adjust slow wave activity in the subject while the subject is asleep during the current sleep session and/or while the subject is awake before the current sleep session such that the sleep session duration meets the sleep session duration target for the current sleep session.

In some embodiments, operation 708 is performed by sensory stimulators and a computer program module the same as or similar to sensory stimulators 16 and control module 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to manage a sleep session of a subject, the system comprising:
one or more sensory stimulators configured to provide sensory stimuli to the subject;
one or more sensors configured to generate output signals conveying information related to a current sleep stage of the subject during the sleep session; and
one or more processors configured by machine-readable instructions to:
determine a dissipation threshold level for triggering a sensory waking stimulus;
obtain, during the sleep session, the output signals from the one or more sensors, at least some of the output signals being related to slow wave activity in the subject;
monitor, during the sleep session, the slow wave activity based on the output signals;
determine, based on the monitoring of the slow wave activity, a rate of change in the slow wave activity over time with respect to the sleep session;
determine a sleep pressure dissipation level of the subject based on the rate of change in the slow wave activity, the sleep pressure dissipation level being a metric indicating a level of dissipation with respect to sleep pressure of the subject, the sleep pressure indicating the subject's remaining need for sleep; and
responsive to the sleep pressure dissipation level breaching the dissipation threshold level, control the one or more sensory stimulators to generate the sensory waking stimulus to cause the subject to wake from the sleep session.

2. The system of claim 1, wherein the one or more processors are configured to determine the dissipation threshold level based on information from one or more previous sleep sessions of the subject.

3. The system of claim 1, further comprising a user interface configured to receive information related to a sleep session duration target for the subject;
wherein the one or more sensory stimulators are configured to provide sensory stimulation separate from the sensory waking stimulus to the subject during the sleep session to adjust the slow wave activity in the subject; and
wherein the one or more processors are configured to control the one or more sensory stimulators to adjust the slow wave activity in the subject such that a sleep session duration meets the sleep session duration target, the one or more processors configured to control the one or more sensory stimulators based on the sleep session duration target, the determined sleep pressure dissipation level, and the dissipation threshold level.

4. The system of claim 3, wherein the one or more processors are configured to provide the sensory stimulation separate from the sensory waking stimulus to the subject during the sleep session to increase and/or decrease the slow wave activity in the subject such that controlling the one or more sensory stimulators to increase the slow wave activity in the subject results in faster sleep pressure dissipation and an increase in the sleep pressure dissipation level, and controlling the one or more sensory stimulators to decrease the slow wave activity in the subject results in slower sleep pressure dissipation and a decrease in the sleep pressure dissipation level.

5. The system of claim 3, wherein the one or more processors are configured to control the one or more sensory stimulators to provide the sensory stimulation separate from the sensory waking stimulus to the subject to adjust the slow wave activity in the subject while the subject is asleep during the sleep session and/or while the subject is awake before the sleep session such that the sleep session duration meets the sleep session duration target for the sleep session.

6. A method for managing a sleep session of a subject with a management system, the system comprising one or more sensory stimulators, one or more sensors, and one or more processors configured by machine-readable instructions, the method comprising:
   generating output signals conveying information related to a current sleep stage of the subject during the sleep session with the one or more sensors;
   determining, with the one or more processors, a dissipation threshold level for triggering a sensory waking stimulus;
   obtaining, with the one or more processors, during the sleep session, the output signals from the one or more sensors, at least some of the output signals being related to slow wave activity in the subject;
   monitoring, with the one or more processors, during the sleep session, the slow wave activity based on the output signals;
   determining, with the one or more processors, based on the monitoring of the slow wave activity, a rate of change in the slow wave activity over time with respect to the sleep session;
   determining, with the one or more processors, a sleep pressure dissipation level of the subject based on the rate of change in the slow wave activity, the sleep pressure dissipation level being a metric indicating a level of dissipation with respect to sleep pressure of the subject, the sleep pressure indicating the subject's remaining need for sleep; and
   responsive to the sleep pressure dissipation level breaching the dissipation threshold level, controlling, with the one or more processors, the one or more sensory stimulators to generate the sensory waking stimulus to cause the subject to wake from the sleep session.

7. The method of claim 6, further comprising determining, with the one or more processors, the dissipation threshold level based on information from one or more previous sleep sessions of the subject.

8. The method of claim 6, further comprising receiving information related to a sleep session duration target for the subject via a user interface;
   providing sensory stimulation separate from the sensory waking stimulus to the subject with the one or more sensory stimulators during the sleep session to adjust the slow wave activity in the subject; and
   controlling, with the one or more processors, the one or more sensory stimulators to adjust the slow wave activity in the subject such that a sleep session duration meets the sleep session duration target, the controlling based on the sleep session duration target, the determined sleep pressure dissipation level, and the dissipation threshold level.

9. The method of claim 8, wherein controlling, with the one or more processors, the one or more sensory stimulators to provide the sensory stimulation separate from the sensory waking stimulus to the subject during the sleep session to adjust the slow wave activity in the subject comprises controlling the one or more sensory stimulators to increase and/or decrease the slow wave activity in the subject such that controlling the one or more sensory stimulators to increase the slow wave activity in the subject results in faster sleep pressure dissipation and an increase in the sleep pressure dissipation level, and controlling the one or more sensory stimulators to decrease the slow wave activity in the subject results in slower sleep pressure dissipation and a decrease in the sleep pressure dissipation level.

10. The method of claim 8, further comprising controlling, with the one or more processors, the one or more sensory stimulators to provide the sensory stimulation separate from the sensory waking stimulus to the subject to adjust the slow wave activity in the subject while the subject is asleep during the sleep session and/or while the subject is awake before the sleep session such that the sleep session duration meets the sleep session duration target for the sleep session.

11. A system configured to manage a sleep session of a subject, the system comprising:
   means for providing sensory stimuli to the subject;
   means for generating output signals conveying information related to a current sleep stage of the subject during the sleep session;
   means for determining a dissipation threshold level for triggering a sensory waking stimulus;
   means for obtaining, during the sleep session, the output signals from the one or more sensors, at least some of the output signals being related to slow wave activity in the subject;
   means for monitoring, during the sleep session, the slow wave activity based on the output signals;
   means for determining, based on the monitoring of the slow wave activity, a rate of change in the slow wave activity over time with respect to the sleep session;
   means for determining a sleep pressure dissipation level of the subject based on the rate of change in the slow wave activity, the sleep pressure dissipation level being a metric indicating a level of dissipation with respect to sleep pressure of the subject, the sleep pressure indicating the subject's remaining need for sleep; and
   means for, responsive to the sleep pressure dissipation level breaching the dissipation threshold level, controlling the means for providing sensory stimuli to generate the sensory waking stimulus to cause the subject to wake from the sleep session.

12. The system of claim 11, wherein the means for controlling is configured to determine the dissipation threshold level based on information from one or more previous sleep sessions of the subject.

13. The system of claim 11, further comprising means for receiving information related to a sleep session duration target for the subject;
   wherein the means for providing sensory stimuli is configured to provide sensory stimulation separate from the sensory waking stimulus to the subject during the sleep session to adjust the slow wave activity in the subject; and
   wherein the means for controlling is configured to control the means for providing sensory stimuli to adjust the slow wave activity in the subject such that a sleep session duration meets the sleep session duration target, the means for controlling configured to control the one or more sensory stimulators based on the sleep session duration target, the determined sleep pressure dissipation level, and the dissipation threshold level.

14. The system of claim 13, wherein the means for controlling is configured to provide the sensory stimulation separate from the sensory waking stimulus to the subject during the sleep session to increase and/or decrease the slow wave activity in the subject such that controlling the means for providing sensory stimuli to increase the slow wave activity in the subject results in faster sleep pressure dissipation and an increase in the sleep pressure dissipation level, and controlling the means for providing sensory stimuli to decrease the slow wave activity in the subject results in slower sleep pressure dissipation and a decrease in the sleep pressure dissipation level.

15. The system of claim 13, wherein the means for controlling is configured to control the means for providing sensory stimuli to provide the sensory stimulation separate from the sensory waking stimulus to the subject to adjust slow wave activity in the subject while the subject is asleep during the sleep session and/or while the subject is awake before the sleep session such that the sleep session duration meets the sleep session duration target for the sleep session.

* * * * *